United States Patent
Kulah et al.

(10) Patent No.: US 8,480,956 B2
(45) Date of Patent: Jul. 9, 2013

(54) MICROFLUIDIC-CHANNEL EMBEDDABLE, LATERALLY OSCILLATING GRAVIMETRIC SENSOR DEVICE FABRICATED WITH MICRO-ELECTRO-MECHANICAL SYSTEMS (MEMS) TECHNOLOGY

(76) Inventors: Haluk Kulah, Ankara (TR); Ata Tuna Ciftlik, Lausanne (CH)

(*) Notice: Subject to any disclaimer, the term of this patent is extended or adjusted under 35 U.S.C. 154(b) by 0 days.

(21) Appl. No.: 13/391,349

(22) PCT Filed: Aug. 20, 2009

(86) PCT No.: PCT/TR2009/000106
§ 371 (c)(1),
(2), (4) Date: Feb. 20, 2012

(87) PCT Pub. No.: WO2011/021984
PCT Pub. Date: Feb. 24, 2011

(65) Prior Publication Data
US 2012/0148448 A1    Jun. 14, 2012

(51) Int. Cl.
*G01N 33/48*    (2006.01)
(52) U.S. Cl.
USPC ......... 422/68.1; 422/50; 422/82.01; 422/502; 422/503; 436/43; 436/63

(58) Field of Classification Search
USPC .......... 422/50, 68.1, 82.01, 502, 503; 436/43, 436/63
See application file for complete search history.

(56) References Cited

U.S. PATENT DOCUMENTS

| | | | |
|---|---|---|---|
| 2009/0318307 A1* | 12/2009 | Garcia Tello | 506/12 |
| 2012/0301888 A1* | 11/2012 | Neely et al. | 435/6.12 |
| 2013/0029345 A1* | 1/2013 | Neely et al. | 435/6.12 |

* cited by examiner

*Primary Examiner* — Brian J Sines (57) ABSTRACT

Laterally oscillating gravimetric sensing device embeddable under micro-fluidic channels and fabricated with micro-electro mechanical systems (MEMS) technology, which detects biological cells and analytes by measuring the change of mass attached on its surface is composed of four main groups, namely a resonator that can be placed onto the basis of the channel, components of the resonator bio-activation, a micro fluidic channel, and the microfabrication techniques, and its main components are the proof mass (1), comb fingers fixed to proof mass (2), folded spring beams (3), channel floor and mechanical soil (4), stationary electrodes (5), comb fingers attached to the stationary electrodes (6), golden film deposited onto the mass (7), immobilized biologic recognition molecules (8), and micro fluidic channel placed on resonator structure (9).

2 Claims, 6 Drawing Sheets

MICROFLUIDIC-CHANNEL EMBEDDABLE, LATERALLY OSCILLATING GRAVIMETRIC SENSOR DEVICE FABRICATED WITH MICRO-ELECTRO-MECHANICAL SYSTEMS (MEMS) TECHNOLOGY

RELATED FIELD OF THE INVENTION

This invention represents a laterally oscillating gravimetric sensing device embeddable under micro-fluidic channels and fabricated with micro-electro mechanical systems (MEMS) technology, which detects biological cell and analytes by measuring the change of mass attached on its surface.

BACKGROUND OF THE INVENTION

Prior Art

A perturbation in the total mass of a resonating mechanical structure induces a shift in the frequency of the resonance. When combined with the micro-electro-mechanical systems, this method called gravimetric detection, may realize devices that can recognize target molecules or structures in the microscale. Gravimetric detectors are employed in many micro systems for biomedical and chemical applications. These can be found in various applications ranging from cell detection for diagnosis of cancer, AIDS or similar diseases to tests for bioterror agents in the air.

Reported biomedical sensors using gravimetric detection in the literature are realized in cantilever structure. Main drawbacks of cantilever type gravimetric detectors are as follows: 1) Vertical oscillation nature with respect to the large area of the cantilever results in squeeze film damping to be more dominant, and thus leads to a very low quality oscillation (quality factor is a parameter indicating the bandwidth of the oscillation; narrower the bandwidth is, higher the frequency resolution and quality factor is) or prevents the oscillation due to over damping within the liquid. For this reason, these systems operate by first immersing into the liquid, then drying and detecting the frequency difference. Therefore, cantilever method prevents high resolution and on-line monitoring. 2) In order to overcome explained low quality factor problem, mass of the cantilevers is decreased significantly and hence the operating frequency is increased too much. Since electronic methods are insufficient in such large frequencies, expensive optical excitation and read-out methods are needed. 3) Since the targets are attached on the surface area randomly in terms of location, frequency shifts that are observed in cantilever type resonators depend on target attachment sites. This situation usually decreases the quantitative concentration resolution. Even if the targets are attached to the adjacent locations, the frequency shift may be non-linear due to large mass-distribution of thin cantilevers.

The proposed device solves mentioned problems using resonators with comb fingers oscillating laterally. The achievements can be summarized as follows:

1) Since oscillation is lateral, the quality factor of system inside water is quite high. Thus, it is possible to realize online and high resolution detection. 2) Since the quality factor is high enough, it is not required to decrease the mass substantially and oscillation frequencies can be kept relatively low. In addition, these systems operate electromechanically and detection system do not need optical marking and read-out since they can be fabricated with electronic read-out circuit. Consequently, they are stand alone and be fabricated with quite low prices. 3) Targets can be redirected to the attachment surface inside the channel where the devices are embedded. Also, thanks to the proof mass having a four-beam mechanical balance, output changes linearly with respect to quantity but independent of target attachment position. Thus, it is possible to obtain devices with high concentration resolution and reproducibility. 4) Using known fabrication techniques, these devices can be produced together with micro fluidic channel and electronic circuit. In addition, quality factor is kept high by a unique technique used for the fabrication.

The following table compares proposed system with cantilever type gravimetric detectors in recent literature.

TABLE 1

A comparison of proposed device with cantilever type gravimetric detectors in recent literature.

|  | Davilla et. al, 2007 | Gfeller et. al, 2005 | Gupta et. al, 2004 | Ghatkesar et. al, 2003 | Invented Device | |
| --- | --- | --- | --- | --- | --- | --- |
| Reference | [1] | [2] | [3] | [4] | Worst | Best |
| Environment | Water and Air | Humid Air | Air | Air | Liquid | Liquid |
| Operating Frequency | Not reported | 30 kHz to 32 kHz | 1.27 MHz | $13^{th}$, $14^{th}$ and $15^{th}$ harmonics 569, 686, 818 kHz | 565 kHz | 296 kHz |
| Quality Factor | Water < 5, air < 90 | Not reported | For the air 5 | $13^{th}$, $14^{th}$ and $15^{th}$ harmonics 28.5, 29.2 and 30.7 | 16 in water | 86 in water |
| Minimum Sensitivity | 0.63 pg | Not reported | 9.5 pg | 80 pg | $0.77 \frac{ag}{\sqrt{Hz}}$ | $67.68 \frac{ag}{\sqrt{Hz}}$ |
| Detection Type | Laser Doppler Vibrometer | None reported | Laser Doppler Vibrometer | Laser Doppler Vibrometer | CMOS Electronics | CMOS Electronics |

AIMS OF THE INVENTION

This invention is a gravimetric sensor device aimed at biological cell and analyte detection, which oscillates laterally and can be embedded under micro-fluidic channels. The main characteristics of this device are:
- High resolution
- Fast
- Fabricated with low-cost
- Low operating costs
- Lower sample consumption
- CMOS compatible and stand-alone
- Highly reproducible
- Unique, yet can be produced easily using known fabrication technologies
- Small and portable
- Disposable or reusable
- Able to operate without complex and expensive external equipment
- Not requiring optical marking and microscope
- Can be used for cell detection and counting
- Can be used for analyte detection and concentration measurements
- Feedback structure Below are the innovations brought to known technique and state-of-the art by this invention:
- Since the oscillation is lateral, the quality factor within the liquid is quite high. Thus, it is possible to have online and high resolution detection.
- Since the quality factor is high, it is not required to decrease the mass significantly and the oscillation frequencies can be kept relatively low. Low frequency makes it possible to operate within an electronic feed-back control and read-out circuit.
- In addition, these systems operate electromechanically and detection system does not need optical marking and detection since they can be fabricated together with electronic read-out circuit. Thus, they can operate alone and be produced at quite low-cost.
- Targets can be directed to the attachment surface which can be placed inside the channel. Besides, redirection is induced automatically. This improves the resolution compared to the existing cantilever type gravimetrical detectors.
- As proof mass has a four-beam mechanically balanced structure, the output changes linearly and is also independent to attachment position. Thus, it is possible to obtain devices with high concentration resolution and reproducibility.
- Micro fabrication technique used in the device, obtained by making changes unique to the MEMS production technologies with the existing SOI (silicon on insulator) process, makes it possible to place the resonators under micro fluidic channels and to integrate the external micro fluidic connection point easily.
- It operates more efficiently and oscillates with higher quality factor by blocking the analyte or cell suspension fluid inside the micro fluidic channel from leaking between the comb fingers.
- Faster analysis of targets will allow obtaining immediate results, and will accelerate the treatment process being used in measuring the success of existing patient treatment methods. Known expensive and limited diagnosis and analysis methods prevent the doctors from realizing these checks during the treatment process.
- Low-cost production will decrease the diagnosis and treatment costs, and thus improve the access to the product by individuals, hospitals and laboratories. Similarly, low operating costs will decrease fixed and variable costs.
- It will be possible to maintain the surgical interventions at a minimal level, thanks to this detection device that needs few samples to get to the result.
- High reproducibility of the fabrication technique decreases costs in terms of time and money for post production calibration and quality control.
- Being small, portable, disposable, as well as the ability to operate independent of expensive and complex external equipment make it quite easy and practical to integrate this device into remote health centers or military units.
- Since it does not require optical systems, fixed costs required for the operation of this device are further decreased.

DEFINITION OF THE FIGURES

Below are the list of figures prepared and attached for a better explanation of laterally oscillating gravimetric sensing device embeddable under micro-fluidic channels and fabricated with micro-electro mechanical systems (MEMS) technology, which detects biological cell and analytes by measuring the change of mass attached on its surface.

DEFINITION OF THE ELEMENTS (FEATURES/COMPONENTS/PARTS) ON THE FIGURES

Attached are the list of figures prepared for a better explanation of the laterally oscillating gravimetric sensing device embeddable under micro-fluidic channels and fabricated with micro-electro mechanical systems (MEMS) technology, which detects biological cell and analytes by measuring the change of mass attached on its surface. In addition, figures are highlighted with colors, and numbered where needed. Explanation for each numbered part is given below. Yet again, some parts are especially shown on the figures in order to make them clear to understand. U title is used to show the production phases, and step by step latest status is shown instead of numbering.

1—Proof mass
2—Comb Fingers Fixed to Proof Mass
3—Folded spring beams
4—Channel Floor and Mechanical Ground
5—Stationary Electrodes
6—Comb Fingers Attached to the Stationary Electrodes
7—Gold Film deposited on proof mass
8—Immobilized biologic recognition molecules
9—Micro fluidic Channel Placed on Resonator structure
U.1—Silicon Dioxide
U.2—Silicon
U.3—Metal U.4—Polymer
U.5—Metallization
U.6—Metal Shaping through etching
U.7—Resonator definition through Deep Reactive Ion Etching (DRIE)
U.8—Conformal polymer coating for insulation
U.9—Polymer Shaping through dry etching
U.10—Metal Shaping through Metallization and Etching
U.11—Polymer Coating
U.12—Polymer Shaping through Dry etching
U.13—Release via removing underlying Silicone Dioxide by Dry or Wet etching
U.14—Polymer Shaping by Polymer Coating and Dry etching
U.15—Glass top-cap adhesion through Polymer/Polymer Thermal Compression
U.16—Micro fluidic Adapter Integration

DETAILED-DESCRIPTION OF THE INVENTION

The device and the method developed through this invention are basically comprised of four (4) main groups as:
Resonator that is embeddable under microfluidic channel
Components of the bio-activation layer
Micro fluidic channel
Microfabrication technique The resonator that can be placed onto the basis of the channel consists of a proof mass (1), the comb fingers fixed to proof mass (2), folded spring beams (3), channel floor and the mechanical ground (4), the stationary electrodes (5) and the comb fingers attached to the stationary electrodes (6). Channel floor and the mechanical ground (4) are attached to the bulk wafer via silicone dioxide, and they do not move. Folded spring beams (3), proof mass (1) and the comb fingers fixed to proof mass (2), are suspended. Parts of the resonator that can be placed onto the basis of the channel (1, 2, 3, 4, 5, and 6) are made of highly- or moderately-conductive single crystal silicon. The polymer coating (U.4) is made of dielectric polymers coated in such way that the resonator components do not touch each other. All components (1, 2, 3, 4, 5, and 6) are also coated with polymer.

Figure 2:
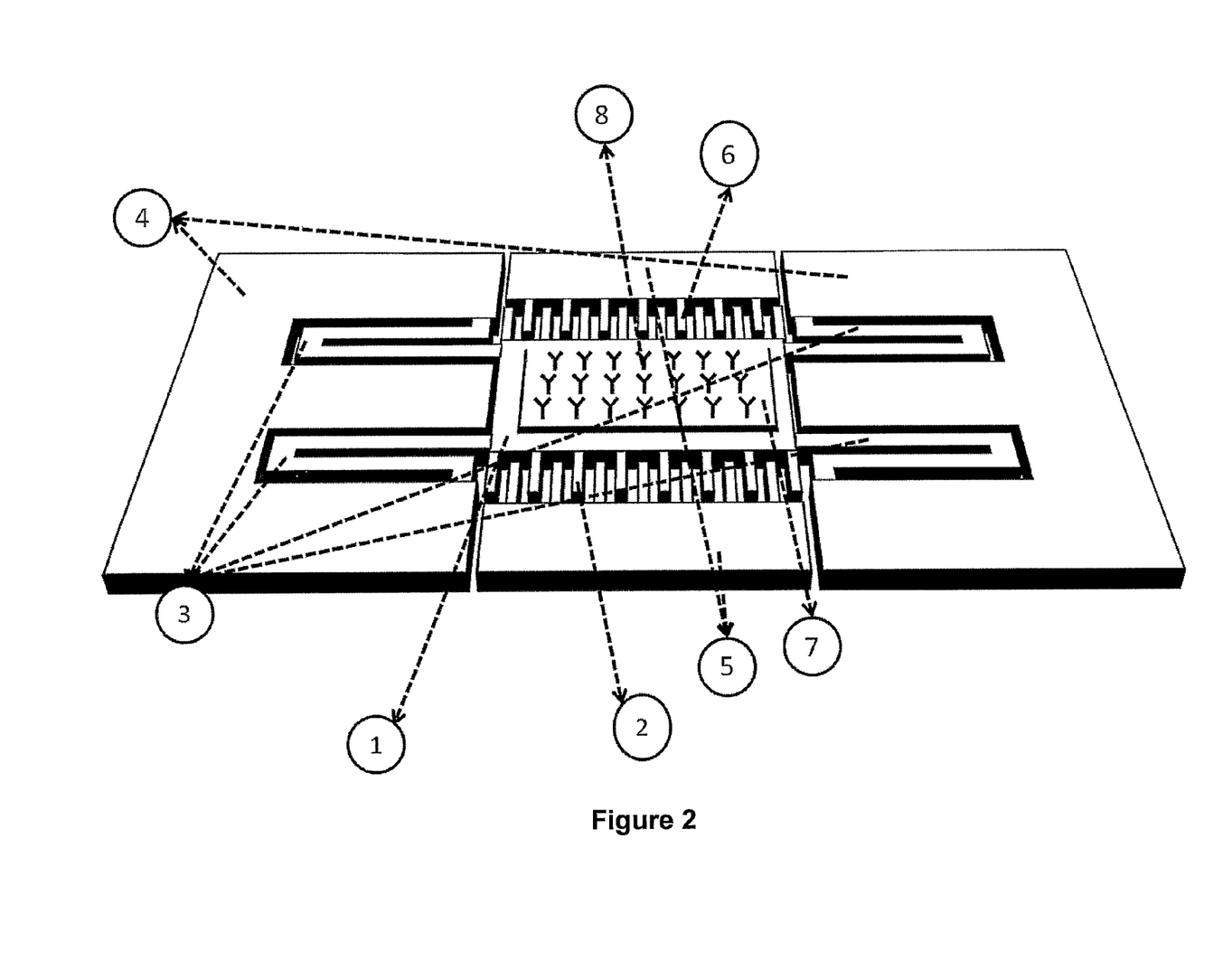
FIG. 2—Perspective view of the resonator that can be placed on the basis of the channel and bio-activation components FIG. 3—Perspective view of the resonator that can be placed on the basis of the channel and the micro fluidic channel FIG. 4—Microfabrication technique, production steps part 1

The components of the resonator bio-activation are comprised of golden film deposited on the proof mass (7) on top of the polymer coated proof mass (1) and immobilized biological recognition molecules (8) attached onto the film using well known protocols.

Figure 3:
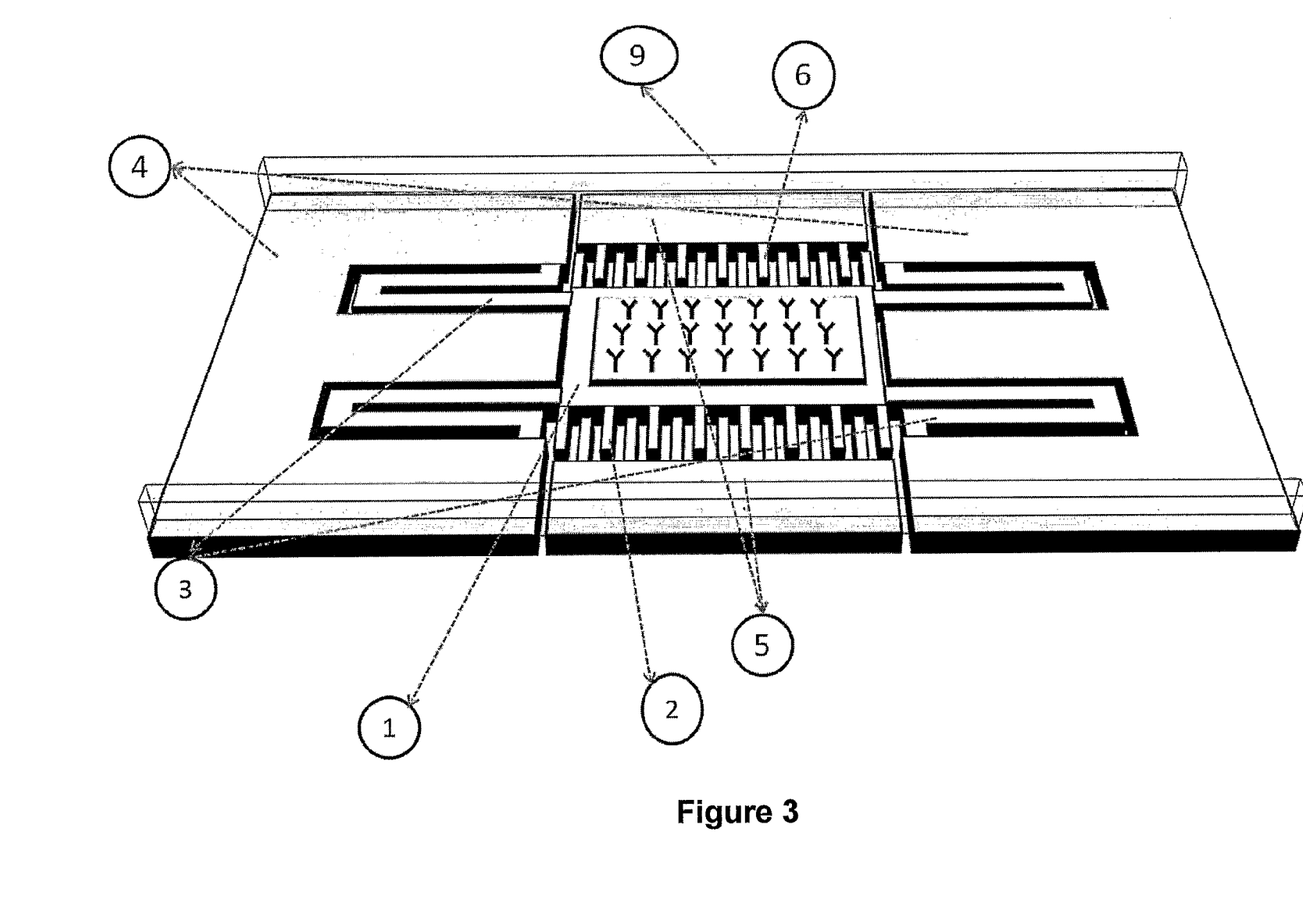

The micro fluidic channel placed on the resonator structure (9) is placed on a larger area compared to the resonator placed on the basis of the channel. Walls and top of the channel are made of transparent polymer or Pyrex. As a result, it will be possible to apply optical methods when complementary techniques are needed for the operation of the device. It is even possible to use the device for other applications by integration of optical reading methods and the resonator.

Figure 4:
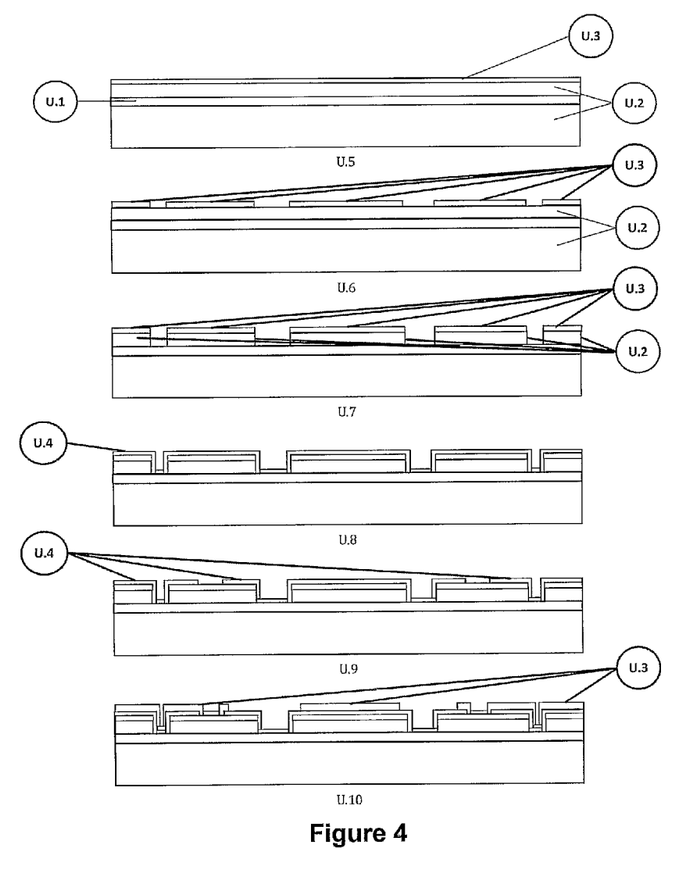
Figure 5:
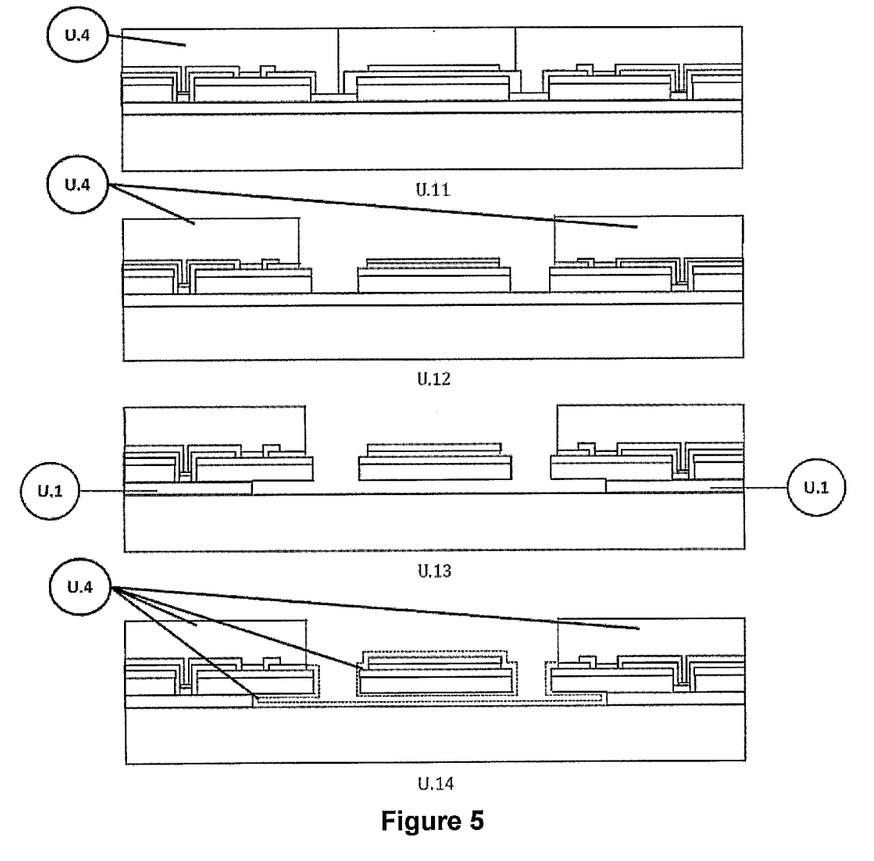
FIG. 5—Microfabrication technique, production steps part 2
Figure 6:
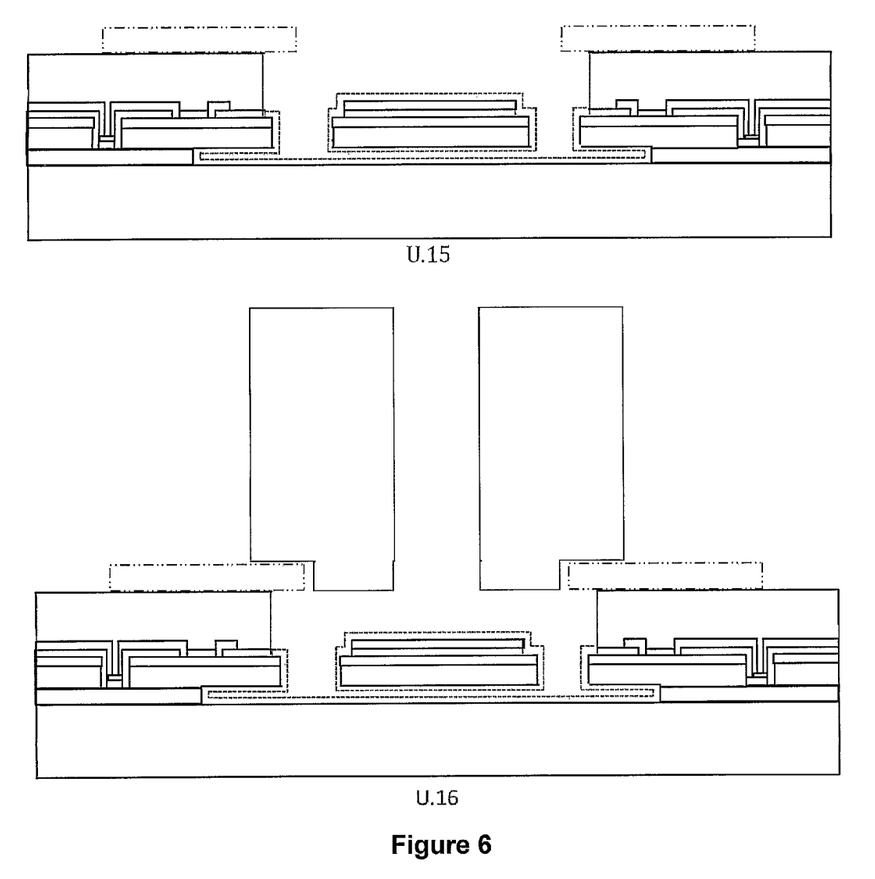
FIG. 6—Microfabrication technique, production steps part 3

Microfabrication technique, using silicon (U.2), silicone dioxide (U.1) and SOI wafers made of silicon (U.2) respectively, and by means of metallization (U.5), Metal Shaping through etching (U.6), Resonator definition through Deep Reactive Ion etching (U.7), Conformal Polymer Coating for Insulation (U.8), Polymer Shaping through Dry etching (U.9), Metal Shaping-through Metallization and etching (U.10), Polymer Coating (U.11), Polymer Shaping through Dry etching (U.12), Release via Lifting Silicone Dioxide through Dry or Wet etching (U.13), Polymer Shaping through Polymer Coating and Dry etching (U.14), Glass Top-Cap Adhesion through Polymer/Polymer Thermal Compression (U.15) and Micro fluidic Adapter Integration (U.16) methods respectively, is comprised of the production of laterally oscillating gravimetric sensing device embeddable under micro-fluidic channels and fabricated with micro-electro mechanical systems (MEMS) technology, which detects biological cell and analytes by measuring the change of mass attached on its surface.

Operation of the System

At the outset, the proof mass (1) and the gold film deposited on proof mass (7) are activated for target recognition by means of those protocols fixating the known biological recognition molecules onto the gold. Through this process, the biological agents having the ability to attach themselves to the target cells or analytes are fixed on the gold film surface in a selective manner.

Figure 1:
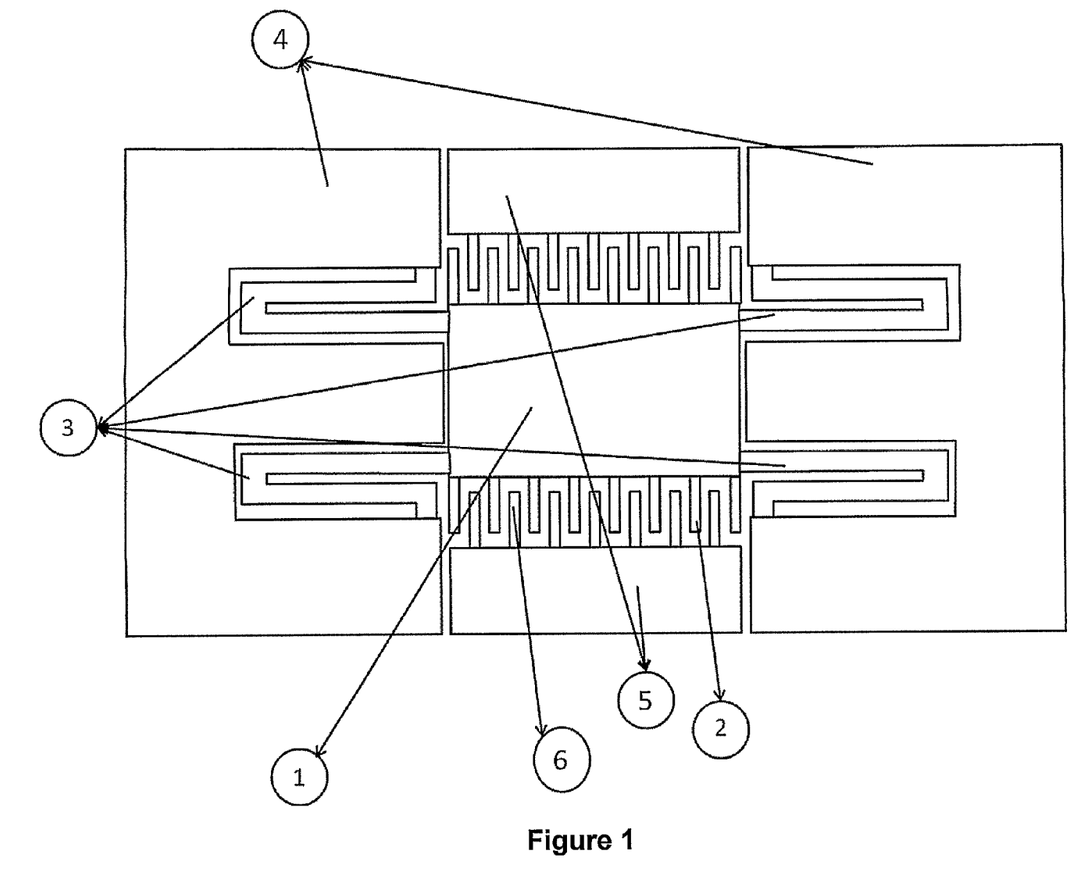
FIG. 1—Top view of the resonator that can be placed on the basis of the channel

After that, the MEMS resonator placed within the channel is oscillated at resonance: The proof mass (1), the comb fingers fixed to proof mass (2), folded spring beams (3), as well as channel floor and the mechanical ground (4) form an electrically connected node, where a voltage is applied from outside via input electrodes created originally in the production phase. The stationary electrodes (5) and the comb fingers attached to the stationary electrodes (6) are connected to the electronic control circuit operated through closed circuit positive feedback. Within this current status of the system, the resonator oscillates laterally in its natural resonance frequency, and at the output of this circuit, an alternative voltage in the resonator's natural resonance frequency is probed.

Following the initialization of the oscillation, samples to be measured are injected into the micro channels by means of micro fluidic adaptors. Resonators placed on the basis of the micro channel in a straightforward manner do not prevent the flow within the micro channels. Simultaneously, frequency of the alternative voltage at the output of the circuit is probed. When a cell or analyte attach to the surface of the proof mass (1), then the frequency of the mechanical resonance and the frequency of the alternative voltage at the circuit output changes. The change in frequency is proportional to the target mass attached to the surface.

In cell detection applications, the dielectrophoretic forces resulted from the electrical area between the proof mass (1) and the stationary electrodes (5) are directed towards the core of the proof mass (1), and decrease the number of minimum detectable cells by increasing their probability for attachment. In addition, dependence of the proof mass (1) practicing four-faceted lateral oscillation and of the amount of change in frequencies to the cell attachment location is minimized.

The hydrophobic polymer coated between the comb fingers fixed to proof mass (2), the stationary electrodes (5), the proof mass (1), the channel floor and the mechanical ground (4) and the folded spring beams (3) puts off a liquid leakage among these components, decreases the friction coefficient, and maintains the high quality factor. Additionally, this polymer layer prevents a direct contact between conducting biological liquids and the resonator that can be placed on the basis of the channel, and ensures the electromechanical oscillation. Furthermore, this polymer film coated onto the surfaces increases the effective dielectrical constant between the comb fingers fixed to proof mass (2) and has an impact increasing the electromechanical gain.

Table 2 shows the operating frequency, quality factor and noise equivalent mass difference (NEMD) of the devices that are the subject of this invention. Various devices indicated with 'RCD' are same devices fabricated of different microfabrication parameters. The highest and the lowest values are highlighted with bold letters. Table 1 gives a comparison of these values to their similar ones recently published.

TABLE 2

Operating frequency, quality factor and noise equivalent mass difference (NEMD) of the devices being the subject of this invention

| Name | Working Frequency (kHz) | Quality Factor | NEMD |
|---|---|---|---|
| RCD1.1 | 799 | 24 | 1.01 |
| RCD1.2 | 565 | 16 | 2.00 |
| RCD1.3 | 804 | 28 | 1.18 |
| RCD1.4 | 586 | 21 | 2.00 |
| RCD2.1 | 2278 | 68 | 0.77 |
| RCD2.2 | 795 | 38 | 1.08 |
| RCD2.3 | 566 | 33 | 1.53 |
| RCD2.4 | 415 | 30 | 4.03 |
| RCD2.5 | 284 | 21 | 7.91 |
| RCD2.6 | 2279 | 61 | 1.29 |
| RCD2.7 | 794 | 36 | 1.77 |
| RCD2.8 | 568 | 31 | 2.51 |
| RCD2.9 | 411 | 34 | 4.76 |
| RCD2.10 | 296 | 34 | 5.67 |
| RCD3.1 | 1179 | 60 | 5.73 |
| RCD3.2 | 830 | 42 | 11.25 |
| RCD3.4 | 293 | 29 | 11.41 |
| RCD3.5 | 1609 | 58 | 2.91 |
| RCD3.6 | 1190 | 86 | 4.82 |
| RCD3.7 | 846 | 72 | 7.76 |
| RCD3.8 | 296 | 42 | 67.68 |
| Average | 876 | 42 | 6.9 |

REFERENCES

[1] A. P. Davila, J. Jang, A. K. Gupta et al., "Microresonator mass sensors for detection of *Bacillus anthracis* Sterne spores in air and water," *Biosens Bioelectron*, vol. 22, no. 12, pp. 3028-35, Jun. 15, 2007.

[2] K. Y. Gfeller, N. Nugaeva, and M. Hegner, "Micromechanical oscillators as rapid biosensor for the detection of active growth of *Escherichia coli*," *Biosens Bioelectron*, vol. 21, no. 3, pp. 528-33, Sep. 15, 2005.

[3] A. Gupta, D. Akin, and R. Bashir, "Single virus particle mass detection using microresonators with nanoscale thickness," *Applied Physics Letters*, vol. 84, no. 11, pp. 1976-1978, 2004.

[4] M. K. Ghalkesar, V. Barwich, T. Braun et al., "Real-time mass sensing by nanomechanical resonators in fluid." pp. 1060-1063 vol. 2.

The invention claimed is:

1. A laterally oscillating gravimetric sensing device being embeddable inside a micro-fluidic channel to detect analytes and/or biological entities by measuring the change of mass attached on its surface, comprising:

a hydrophobic polymer coated proof-mass (1) that can be placed inside a microfluidic channel where the hydrophobic polymer prevents direct contact of proof-mass to the liquid and facilitates electrical actuation and read-out of the proof-mass;

comb-fingers fixed to the proof mass (2) coated with the same hydrophobic polymer for electrical read-out and actuation of the proof mass where the hydrophobic polymer prevents both direct contact of conductive comb-fingers to the liquid and filling of the liquid between comb-fingers for keeping quality factor of oscillation high inside the liquid environment;

stationary electrodes (5) coated with the said hydrophobic polymer for electrical read-out and actuation of the proof mass where the hydrophobic polymer prevents both direct contact of the stationary electrodes (5) to the liquid and filling of the liquid between comb-fingers and stationary electrodes for keeping the quality factor of oscillation high inside the liquid environment; and folded spring beams (3) connecting the proof mass (1) to mechanical ground (4) where this structure minimizes the dependence of the output frequency shift to the mass attachment location.

2. A device as given in claim 1 and further comprises a golden film deposited on top of the polymer coated proof mass (7) together with immobilized biological recognition molecules (8) attached on the said golden film.

* * * * *